(12) United States Patent
Portney

(10) Patent No.: US 6,596,025 B2
(45) Date of Patent: Jul. 22, 2003

(54) NARROW PROFILE INTRAOCULAR LENS

(76) Inventor: Valdemar Portney, 11940 N. Riviera, Tustin, CA (US) 92782

( * ) Notice: Subject to any disclaimer, the term of this patent is extended or adjusted under 35 U.S.C. 154(b) by 16 days.

(21) Appl. No.: 09/809,152

(22) Filed: Mar. 15, 2001

(65) Prior Publication Data
US 2002/0161435 A1 Oct. 31, 2002

(51) Int. Cl.[7] ................................................. A61F 2/16
(52) U.S. Cl. ................... 623/6.17; 623/6.15; 623/6.18; 623/6.19; 623/6.25
(58) Field of Search .......................... 623/6, 6.11, 6.15, 623/6.17, 6.19, 6.23, 6.25–6.31, 6.37; 351/160, 161, 163

(56) References Cited

U.S. PATENT DOCUMENTS

| | | | |
|---|---|---|---|
| 3,004,470 A | * 10/1961 | Ruhle | |
| 4,340,283 A | 7/1982 | Cohen | |
| 4,561,736 A | * 12/1985 | Furter et al. | 351/159 |
| 4,580,882 A | * 4/1986 | Nuchman et al. | 351/161 |
| 4,637,697 A | 1/1987 | Freeman | |
| 4,673,406 A | 6/1987 | Schlegel | |
| 4,703,405 A | * 10/1987 | Lewin | 362/333 |
| 4,787,903 A | 11/1988 | Grendahl | |
| 4,846,833 A | 7/1989 | Cumming | |
| 4,861,140 A | * 8/1989 | Lucitte et al. | 350/320 |
| 4,881,805 A | * 11/1989 | Cohen | 351/161 |
| 4,995,715 A | * 2/1991 | Cohen | 351/161 |
| 5,054,905 A | 10/1991 | Cohen | |
| 5,056,908 A | * 10/1991 | Cohen | 351/161 |
| 5,120,120 A | * 6/1992 | Cohen | 351/161 |
| 5,121,980 A | * 6/1992 | Cohen | 351/161 |
| 5,178,636 A | 1/1993 | Silberman | |
| 5,201,763 A | * 4/1993 | Brady et al. | 623/6 |
| 5,260,727 A | * 11/1993 | Oksman et al. | 351/162 |
| 5,476,513 A | * 12/1995 | Brady et al. | 623/6 |
| 5,507,806 A | * 4/1996 | Blake | 623/6 |
| 5,699,142 A | 12/1997 | Lee | |
| 5,755,786 A | * 5/1998 | Woffinden et al. | 623/15 |
| 5,760,871 A | * 6/1998 | Kosoburd et al. | 351/161 |
| 6,015,435 A | * 1/2000 | Valunin et al. | 623/6 |
| 6,096,077 A | 8/2000 | Callahan et al. | |
| 6,162,249 A | * 12/2000 | Deacon et al. | 623/6.16 |

OTHER PUBLICATIONS

Analysis of Edge Glare Phenomena in Intraocular Lens Edge design Journal of Refractive Surgery vol 25, 1999, pp. 748–752.

* cited by examiner

Primary Examiner—Bruce Snow
Assistant Examiner—Cheryl Miller
(74) Attorney, Agent, or Firm—Howard R. Lambert

(57) ABSTRACT

A narrow profile, glare reducing, refractive mono-focal intraocular lens is described that comprises an optic having an anterior surface and a posterior surface and an optical axis. One of the anterior and posterior surfaces is formed having two adjacent peri-axial, stepped imaging zones, the two imaging zones having the substantially the same optical power that is preferably outside the −5 to +5 diopter range. A transition zone between the two imaging zones preferably has a continuously variable surface curvature that reduces both indirect glare (caused by light refraction) and direct glare (caused by light diffraction) in an individual's eye in which the intraocular lens is implanted. The transition zone surface may alternatively be continuously curved or variably curved to reduce direct glare and indirect glare, respectively. Attachment members joined to the optic position the intraocular lens in an eye with the optical axis of the optic generally aligned with the optical axis of the eye.

16 Claims, 4 Drawing Sheets

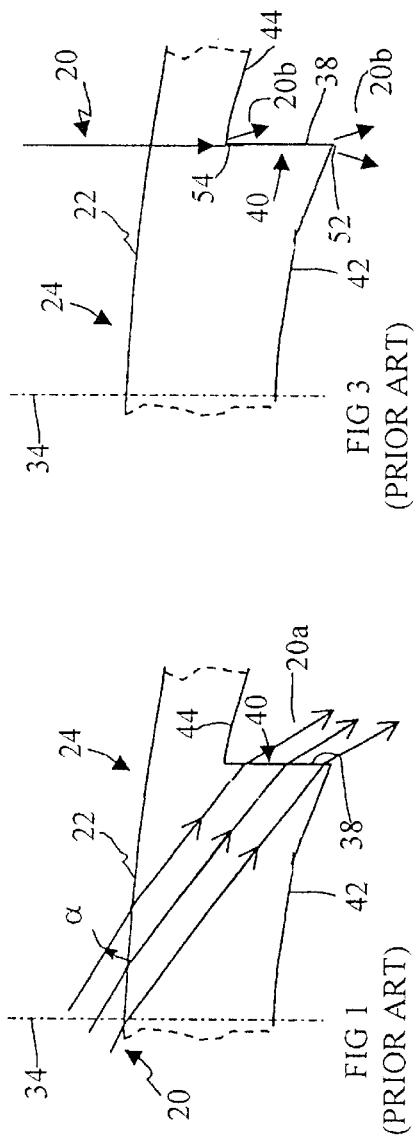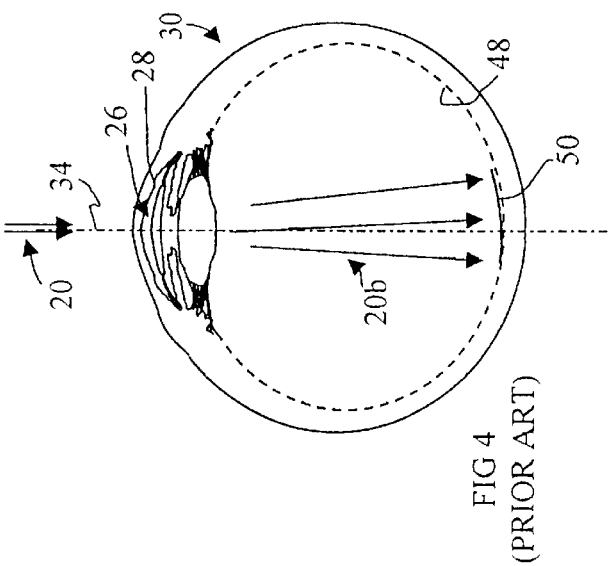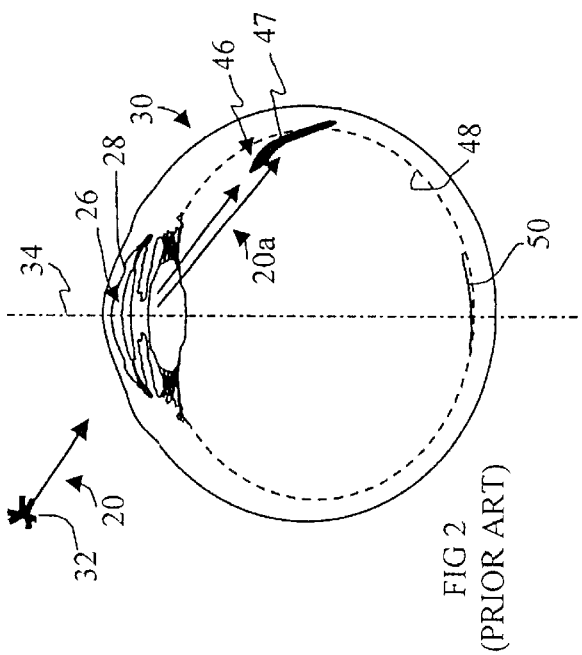

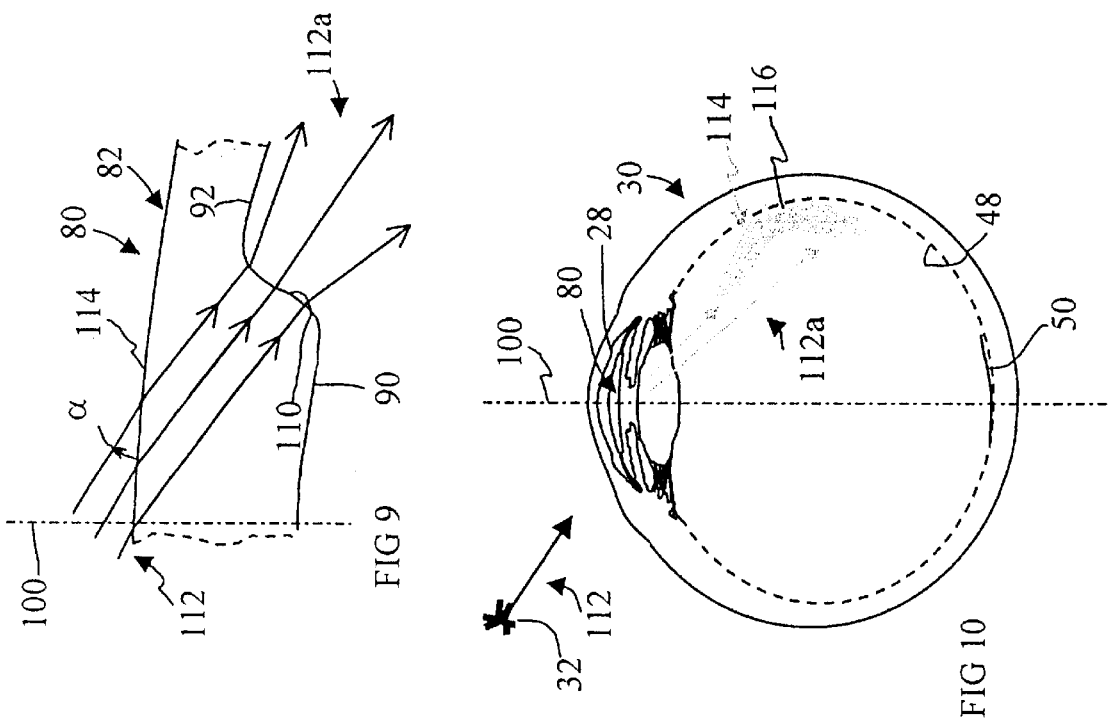
FIG 9
FIG 10
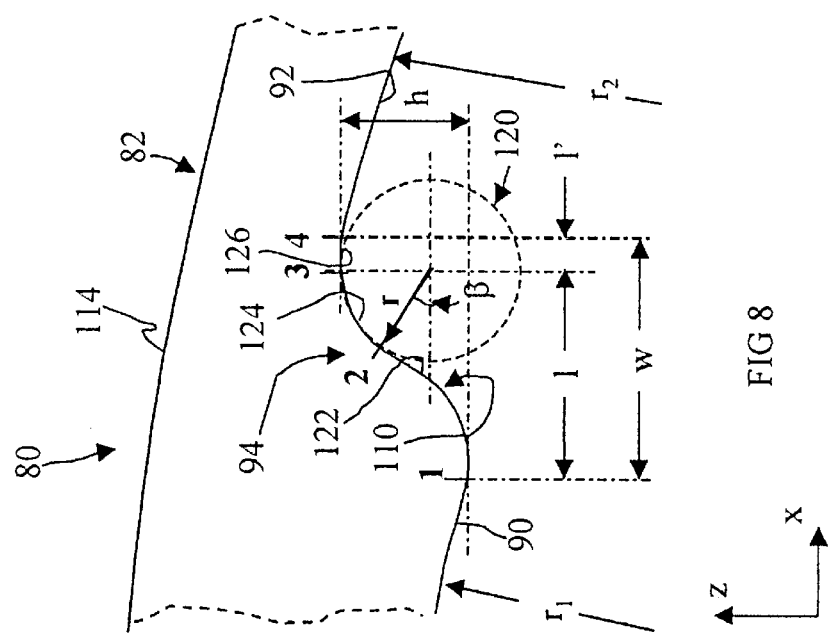
FIG 8

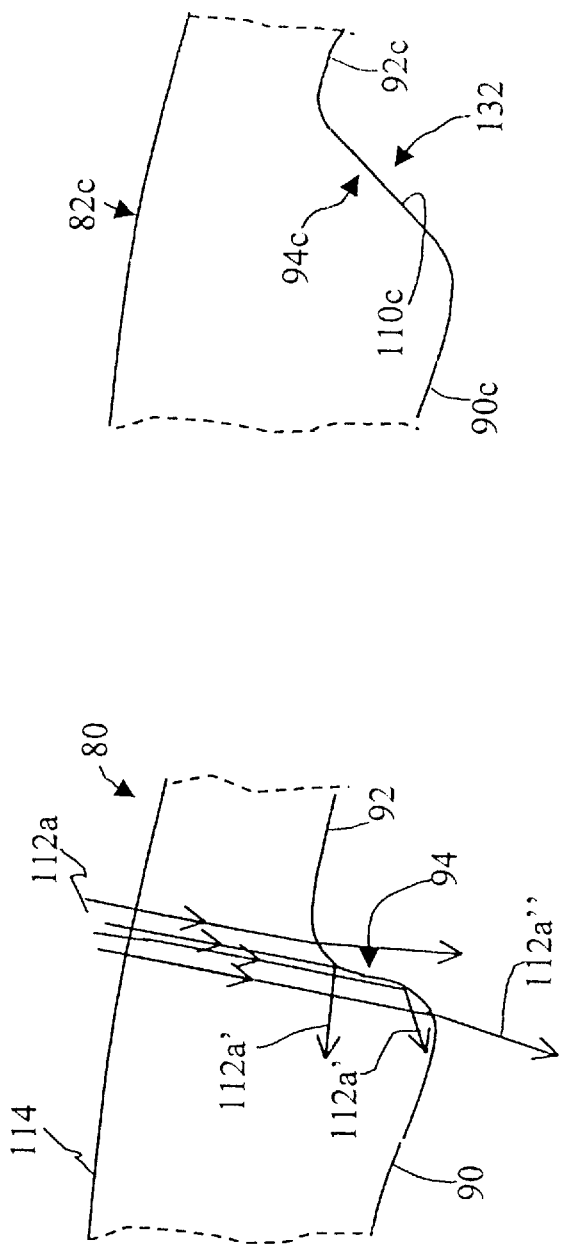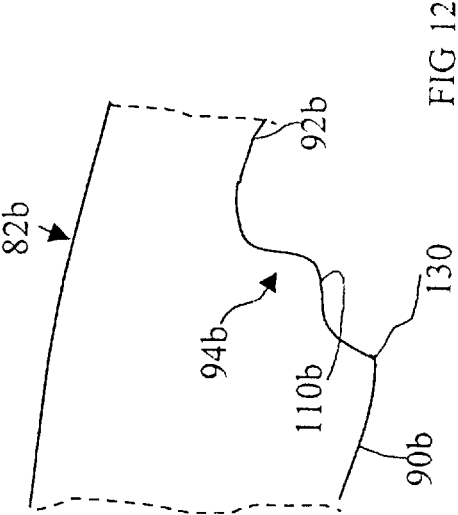

NARROW PROFILE INTRAOCULAR LENS

BACKGROUND OF THE INVENTION

1. Field of the Invention

The present invention relates generally to the field of ophthalmic devices, more particularly to intraocular lenses (IOLs), and still more particularly to thin profile monofocal refractive IOLs for implanting in narrow ocular regions, especially the anterior chamber of an eye.

2. Background Discussion

The following definitions are considered helpful to the understanding of the present invention:

The term "phakic" applies to an eye in which the natural crystalline lens is still present.

The term "aphakic" applies to an eye from which the natural crystalline lens has been surgically removed, for example, due to the formation of cataracts on the lens.

The anterior chamber of an eye is the narrow region between the back, endothelial surface of the cornea and the front surface of the iris.

The posterior chamber of a phakic eye is the narrow region between the back surface of the iris and the front surface of the natural crystalline lens.

A Fresnel lens (as defined at page 167 of the DICTIONARY OF OPTICS, published by Butterworth Heinemann, 1995) is "A lens surface of narrow concentric rings or prism sections of a specified power that gives the effect of a continuous lens surface with the same power, but without the usual thickness and weight."

Glare (as defined at page 53 of THE GLOSSARY OF OPTICAL TERMINOLOGY, published by Professional Press Books, Fairchild Publications, 1986) is "Any degree of light falling on the retina in excess of that which enables one to see clearly." And alternatively as "Any excess of light which hinders rather than helps vision. (Too much light in the wrong place.)"

Vision in a phakic eye is caused by light from a viewed object being refracted by the cornea and the natural crystalline lens to form an image on the retina at the back of the eye. Corrective spectacles, contact lens or corneal reshaping may be used to assist such image formations Optical muscles connected to a normal crystalline lens change the shape of the lens as needed to provide images of objects at different distances from the eye, an optical process known as accommodation.

The prevailing procedure for restoring vision (except for accommodation) in an aphakic eye is the surgical implanting of a refractive artificial lens, called an intraocular lens (IOL), ordinarily in the capsular bag from which the natural lens has been removed.

In addition to continued development of IOLs for restoring vision in aphakic eyes, considerable attention has recently been directed toward developing refractive IOLs (and insertion instruments) for implanting in the anterior chamber of phakic eyes having normal crystalline lenses to correct such vision defects as myopia, hypermetropia, presbyopia and astigmatism. The implanting of such corrective IOLs can potentially eliminate the wearing of spectacles or contact lenses, and/or eliminate permanent surgical procedures involving the cornea.

Anterior chamber-type IOLs may alternatively be implanted in posterior chambers of phakic eyes for providing corrective power to the natural lens, as may be needed due to subsequent physiological changes of the natural lens as an individual ages.

The anterior chamber is generally dome-shaped and very narrow—typically only about 3 mm at its center. The posterior chamber of a phakic eye be even more narrow, depending upon the size of the crystalline lens and the amount of its accommodation the width of the posterior chamber of a phakic eye—the successful implanting of a corrective IOL in either of these ocular chambers is extremely difficult and risks injuring delicate ocular tissue, especially the cornea's endothelial surface in the case of anterior chamber implanting. Consequently, refractive corrective IOLs, particularly the IOL optics, are desirably made as thin as possible consistent with providing the requisite corrective power and structural stability of the optic.

To this end, several known patents disclose the use of a Fresnel lens on one surface of a refractive IOL optic. For example, U.S. Pat. No. 4,673,406 to Schiegel (issued Jun. 16, 1987) discloses a one-piece foldable refractive IOL with one surface of its central lens body formed as a Fresnel lens to reduce the thickness of the optic to enable the IOL to be implanted in a folded condition into an eye through a small corneal incision. The patent further discloses that individual zones of the multi-zone Fresnel lens are selected such that the focal points of all the zones coincide so as to reduce spherical aberration.

As another example, U.S. Pat. No. 4,787,903 to Grendahl (issued Nov. 29, 1988) discloses a refractive IOL or corneal lens having an optic that incorporates a Fresnel lens with multiple, concentric ring-zones. The Grendahl lens is further disclosed as being made of a composite material that allows refractive index modification with electromagnetic energy. (The Grendahl patent asserts a first use of a Fresnel lens for IOLs or corneal lenses, the Grendahl patent application having been filed shortly before the Schiegel patent application was filed).

As still further examples, U.S. Pat. No. 4,846,833 to Cumming (issued Jul. 11, 1989) discloses the forming of a Fresnel lens on the back surface of a posterior chamber IOL so the Fresnel surface will be sealed by the posterior capsule surface upon the implanting of the IOL in an aphakic eye. U.S. Pat. No. 6,096,077 to Callahan et al. (issued Aug. 1, 2000) discloses a thin IOL having the posterior surface formed of a stepped series of annular concentric rings of increasing diameter surrounding a central planar disc region; although, the Callahan et al. patent does not specifically identify the IOL posterior surface as being a Fresnel lens, the associated figures indicate that such is the case.

A characteristic common to the four above-cited patents is that the Fresnel zones comprise a series of staircase-like concentric zones separated from one another by abrupt transition steps. None of the Specifications of the cited patents describe these transition steps, however the accompanying figures depict the transition steps as having flat transition surfaces that are parallel to one another and to the optical axis of the optic, as are all Fresnel lenses. Moreover, none of the above-cited patents disclose any glare effects that may be caused by the flat transition steps between Fresnel zones.

As shown below by the present inventor, IOLs having abrupt Fresnel zone transition steps with flat surfaces induce substantial distracting and potentially hazardous glare in the IOL wearer's eye when light (especially bright light) impinges on the lens optic as, for example, is commonly encountered in night driving or when driving into the sun.

Accordingly, a principal objective of the present invention is to provide a narrow profile (that is, thin) IOL, in particular, a narrow profile monofocal IOL that substantially minimizes such visual glare problems.

SUMMARY OF THE INVENTION

In accordance with the present invention, a narrow profile, glare reducing refractive monofocal intraocular lens comprises an optic having an anterior surface and a posterior surface and an optical axis. One of the anterior and posterior surfaces is formed having adjacent first and second peri-axial, stepped imaging zones, the second peri-axial imaging zone having the substantially the same optical power as the first peri-optical imaging zone.

A transition zone between the first and second peri-axial imaging zones is preferably formed having a surface of continuous variable curvature so as to reduce both indirect glare (caused by refraction) and direct glare (caused by diffraction) in an individual's eye in which the intraocular lens is implanted from light impinging on the optic.

Positioning means are joined to the optic for positioning the intraocular lens in the eye with the optical axis of the optic generally aligned with the optical axis of the eye.

The first peri-axial imaging zone may be circular in shape and be centered at the optical axis of the optic and may have a diameter between about 4.3 mm and about 4.5 mm. The second peri-axial imaging zone is in such case formed in annular ring around the first peri-axial imaging zone.

The first peri-axial imaging zone may be recessed in the optic relative to the second peri-axial imaging zone. Alternatively, the second peri-axial imaging zone may be recessed in the optic relative to the first peri-axial imaging zone.

In combination, the first and second peri-axial imaging zones and the transition zone define one surface, preferably the posterior surface, of the optic that has a preferred maximum thickness at any point of between about 0.30 mm and about 0.40 mm. Also the optical power of the peri-axial transition zones is preferably outside the diopter range of about −5 to about +5.

Still preferably, the height of the transition zone, the surface of which may be generally S-shaped, is preferably between about 0.10 mm and about 0.40 mm and the width of the transition zone is preferably between about 0.15 mm and about 0.30 mm.

In one variation intraocular lens, the transition zone surface has a continuous curvature that eliminates glare caused by diffraction and in another variation intraocular lens the transition zone has a surface of variable curvature that that reduces glare caused by refraction.

BRIEF DESCRIPTION OF THE DRAWINGS

The present invention can be more readily understood by a consideration of the following detailed description when taken in conjunction with the accompanying drawings, in which:

FIG. 1 is a partial cross sectional drawing of a representative prior art refractive intraocular lens employing a Fresnel lens on one surface of the optic, showing a sharp, flat step between a representative pair of adjacent Fresnel zones, showing several light rays obliquely incident on the front surface of the optic and showing the path of the light rays as they are refracted through the optic and out through the flat Fresnel zone step surface;

FIG. 2 is a cross sectional drawing of an eye in which the representative intraocular lens of FIG. 1 is implanted in the anterior chamber, and depicting a typical strong indirect glare pattern formed on a peripheral region of the eye's retina by the light rays that are obliquely incident on the sharp, flat Fresnel zone step as depicted in FIG. 1;

FIG. 3 is a partial cross sectional drawing, similar to FIG. 1, of a representative prior art refractive intraocular lens employing a Fresnel lens on one surface of the optic, showing a sharp, flat step between a representative pair of adjacent Fresnel zones, showing a single light ray perpendicularly incident on the front surface of the optic and showing the path of the light ray as it is refracted through the optic and is diffracted out of the optic at sharp corners of the sharp, flat Fresnel zone step surface;

FIG. 4 is a cross sectional drawing of an eye, similar to FIG. 2, in which the representative intraocular lens of FIG. 3 is implanted in the anterior chamber, and depicting the manner in which a direct glare pattern is formed at the image region of the retina by the diffracted light from the intraocular lens Fresnel zone step as depicted in FIG. 3;

FIG. 8 is a an enlarged cross section of the transition zone of the intraocular lens optic of FIG. 6, showing the shape of a continuously variable curvature of the transition zone surface;

FIG. 9 is a cross sectional drawing similar to FIG. 8, depicting several light rays obliquely incident on the intraocular lens optic and showing the diverging of the light rays refracted by the optic through the transition zone surface;

FIG. 10 is a cross sectional drawing of an eye, similar to FIG. 2, showing a diffuse indirect glare region caused by the light rays diverging from the transition zone surface as depicted in FIG. 9;

FIG. 11 is a cross sectional drawing similar to FIG. 9, depicting several direct light rays incident on the intraocular lens optic and depicting the redirecting of light out of the image by utilization of internal reflection at the transition zone surface;

FIG. 12 is an enlarged cross sectional drawing, corresponding generally to FIG. 8, of a second variation transition zone of the intraocular lens optic of FIG. 6, showing the shape of a transition zone surface of variable curvature (instead of continuously variable curvature); and FIG. 13 is an enlarged cross sectional drawing, corresponding generally to FIG. 8, of a variation transition zone of the intraocular lens optic of FIG. 6, showing the shape of a transition zone surface of continuous curvature (instead of continuously variable curvature).

In the various FIGS. the same elements and features are given the same reference numbers while corresponding features and elements are given the same reference number followed by the letters "a", "b", "c" and so forth as will be apparent.

DESCRIPTION OF THE PREFERRED EMBODIMENT

Figure 7:
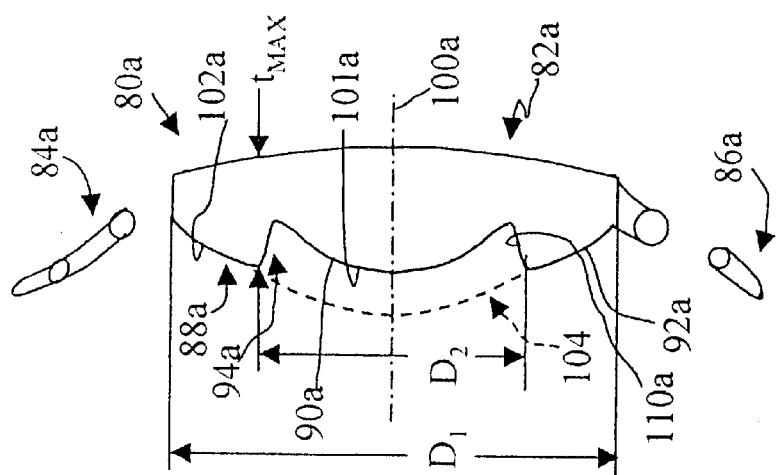
FIG. 7 is a longitudinal cross sectional view corresponding to FIG. 6, showing a variation optic as a bi-convex optic, showing the first and second imaging zones and the transition zone therebetween forming the posterior surface of the optic, showing the first, central, imaging zone recessed into the optic relative to the second imaging zone and showing in phantom lines the thicker shape that the optic would be without the recessed first imaging zone.

Glare caused by abrupt flat transition steps between Fresnel zones of lenses as disclosed in the above-cited patents, may be indirect, direct, or combined indirect and direct, according to lighting conditions encountered by an individual in whose eye the intraocular lens is implanted. Indirect and direct glare are most likely to be encountered at night under driving conditions in which the IOL wearer encounters bright lights, such as streetlights, traffic lights and/or headlights and tail-lights on other vehicles.

FIGS. 1 and 2 illustrate the indirect glare that may, for example, be caused by lights encountered in night driving or by the sun in daylight driving. In FIG. 1, parallel light rays 20 are shown impinging at an oblique angle, α, on a front surface 22 of part of an optic 24 that has a Fresnel lens formed on the back surface. Optic 24 is part of a representative prior art IOL 26 that has been implanted in the anterior chamber 28 of an eye 30 (FIG. 2). Light rays 20 may, for example, originate from a bright streetlight 32 that is out of the direct line of vision 34 of eye 39.

As shown in FIG. 1, light rays 20 are refracted, in accordance with Snell's Law, as they enter, pass through and exit optic 24. Light exits optic 24 as parallel rays 20a from a flat surface 38 of an abrupt Fresnel zone step 40 between adjacent stepped Fresnel zones 42 and 44. Similar oblique light refraction will occur at other abrupt, flat step surfaces (not shown) between other adjacent pairs of Fresnel zones (also not shown). (Viewed image light rays are not shown to avoid confusion.)

Within eye 30 light rays 20a refracted from flat Fresnel zone step surface 38 (as well as light rays refracted from other abrupt flat Fresnel zone step surfaces) of optic 24 impinge on a region 46 of retina 48 (shown in broken lines) to cause a bright glare pattern 47 (indicated by a bold, dark shading). The location of retinal glare pattern 47 depends upon the oblique light angle, α, of incidence on optic 24, but is typically outside a normal viewed image region 50 of retina 48 in a light-sensitive rod region of the retina.

Indirect glare, especially sudden bright glare, in peripheral retinal region 46 can be extremely distracting to the individual in which IOL 26 is implanted, and in night driving can cause driver confusion and make driving dangerous.

Furthermore, as depicted in FIGS. 3 and 4, sharp corners 52 and 54 of Fresnel zone step 40 (and sharp corners of other Fresnel zone steps of optic 24) cause direct (diffractive) glare. As an illustration, a single light ray 20 shown in FIG. 3 impinging perpendicularly on front surface 22 of optic 24 is diffracted into diverging rays 20b by sharp corners 52 and 54 of representative Fresnel zone step 40 between Fresnel zones 42 and 44. Added light diffraction is caused by corresponding sharp corners of other Fresnel zone steps between other adjacent pairs of Fresnel zones (not shown) of optic 24. (Viewed image light rays are not shown to avoid confusion.)

Scattered rays 20b in eye 30 that impinge on vision region 50 of retina 48 (FIG. 4) cause, most noticeably at night, visual light effects around or at viewed street, traffic, vehicle and other bright lights. These light effects may, for example, be in the form of bright star bursts, streamers or halos (not shown), depending upon ambient light conditions causing the diffractive light scattering by corners of Fresnel zone steps of IOL optic 24. At night these light effects caused by light diffraction at corners of abrupt Fresnel zone steps, like step 40, can be extremely distracting and can make driving in busy traffic dangerous due to their image blurring.

Thus, depending upon light conditions, abrupt Fresnel zone step 40 with flat surface 38 on IOL optic 24 may cause either indirect (refractive) or direct (diffractive) glare, or both types of glare at the same time, in eye 30 of an individual in whom IOL 26 is implanted.

As described hereinbelow, the present inventor has determined that such glare can be substantially reduced by forming a non-abrupt, curved transition zone between adjacent imaging zones.

Figure 5:
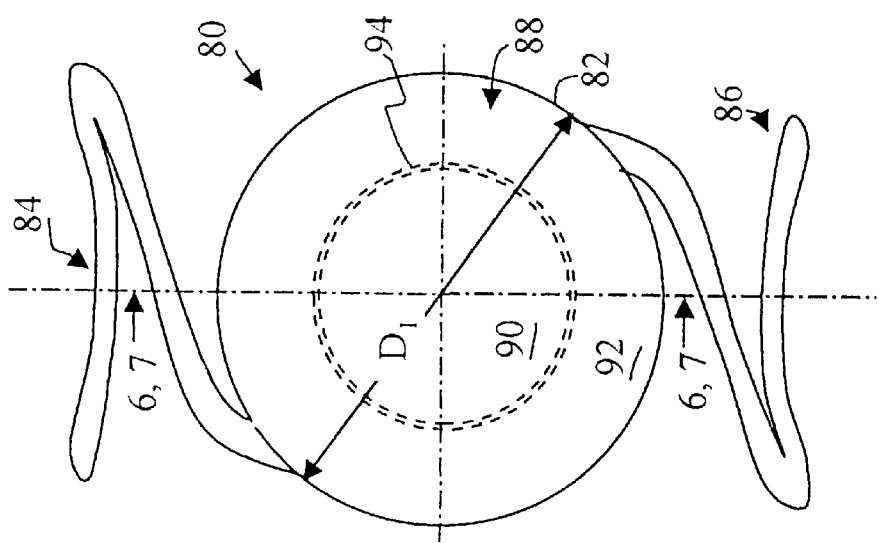
FIG. 5 is a plan view of the posterior (back) surface of an intraocular lens of the present invention, showing the optic and an opposing pair of fixating members, showing a first, central imaging zone surrounded by a second imaging zone, and showing in dashed lines the transition zone between the two imaging zones.

As shown in FIG. 5, a refractive, monofocal intraocular lens 80, according to a preferred embodiment of the present invention, comprises a refractive monofocal optic 82 and first and second positioning (attachment) means or haptics 84 and 86 respectively that are attached or joined to opposite edge regions of the optic. Optic 82, a posterior surface 88 of which is shown, has an outside diameter, $D_1$, which is may, for example, be between about 5.5 mm and about 7.5 mm. Optic 82 is preferably constructed from an elastically deformable material, such as a silicone or acrylic material, to enable the folding of IOL 80 for implanting into an eye through a small ocular incision. Alternatively, optic 82 and haptics 84 and 86 may be formed from poly methyl methacrylate (PMMA).

Figure 6:
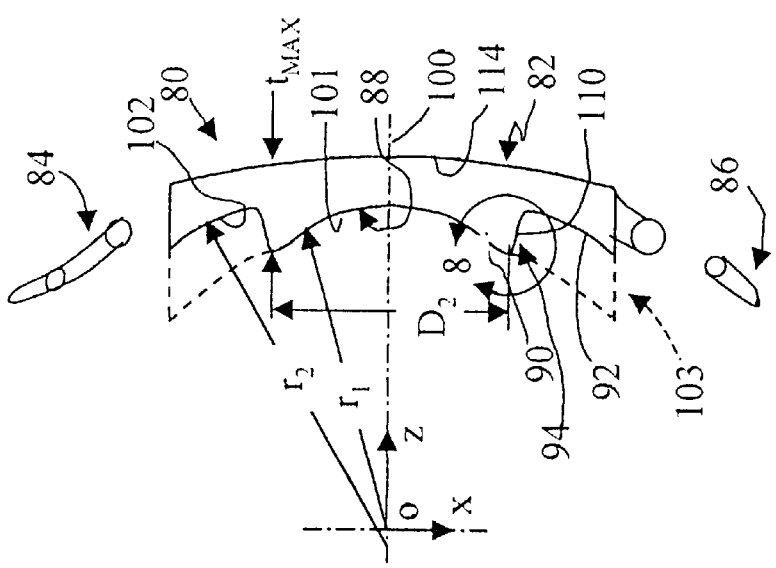
FIG. 6 is a longitudinal cross sectional view looking along line 6—6 of FIG. 5, showing the optic as a concave-convex (meniscus) optic, showing the first and second imaging zones and the transition zone therebetween forming the posterior surface of the optic, showing the second, outer imaging zone recessed into the optic relative to the first, central imaging zone and showing in phantom lines the thicker shape that the optic would be without the recessed second imaging zone.

In the cross sectional drawing of FIG. 6, optic 82 is shown as being of the concave-convex (meniscus) type. Posterior optic surface 88 is formed by respective first and second peri-axial, stepped imaging zones 90 and 92 that are separated by an annular transition zone 94 (shown by broken lines in FIG. 1). Imaging zones 90 and 92 are concentric with an optical axis 100 of optic 82 and both are shaped to have the same optical power, which is preferably outside the diopter range of between about −5 and about +5.

As further shown in FIG. 6, first imaging zone 90 has a preferred diameter, $D_2$, of between about 4.3 mm and about 4.5 mm and has a posterior surface 101 of radius, $r_1$, from an origin, O, located on optical axis 100. Second imaging zone 92 has a posterior surface 102 of radius $r_2$, from coordinate origin, O. Second imaging zone 92 is shown recessed or stepped down relative to first imaging zone 90 with the effect of reducing the peripheral thickness of optic 82, a peripheral optic region 103, (shown in phantom lines) having been eliminated to thereby reduce the preferred maximum thickness, $t_{max}$, of optic 82 at any point to between about 0.3 mm and about 0.4 mm.

Alternatively, as depicted in the cross sectional drawing of FIG. 7, a refractive, monofocal optic 82a of an intraocular lens 80a (that corresponds to above-described intraocular lens 80), is of the bi-convex type. A posterior optic surface 88a is formed by respective first and second peri-axial, stepped imaging zones 90a and 92a that are separated by an annular transition zone 94a (corresponding to first and second imaging zones 90 and 92 and transition zone 94 shown in FIG. 2). Imaging zones 90a and 92a are concentric with an optical axis 100a of optic 82a and respective posterior surface regions 101a and 102a are shaped to have the same optical power, which is preferably outside the diopter range of between about −5 and about +5.

Optic 82*a* has the same outside diameter, $D_1$, that may be between about 5.5 mm and about 7.5 mm, and first imaging zone 90*a* has the same preferred diameter, $D_2$, of between about 4.3 mm and about 4.5 mm. First imaging zone 90*a* is, however, shown recessed or stepped down relative to second imaging zone 92*a*, with the effect of reducing the central thickness of optic 82*a*, a central optic region 104, (shown in phantom lines) having the effect of being eliminated to thereby reduce the preferred maximum thickness, $t_{max}$, of optic 82*a* at any point to between about 0.30 mm and about 0.40 mm.

For both optics 82 and 82*a* the use of only two concentric imaging zones 90, 92 and 90*a*, 92*a*, respectively, is preferred and is considered by the present inventor to provide a sufficiently narrow optic profile for safe implanting of IOLs 80 and 80*a* in anterior chambers of patients, while maintaining IOL optic integrity.

Considering optic 82 as being representative and as described below, the shape of the surface of transition zone 94 between first and second imaging zones 90 and 92 is important for reducing glare in a patient's eye from light impinging on optic 82.

FIG. 8 shows, in an extremely enlarged representation, a preferred, transition zone surface 110 of transition zone 94 between respective first and second imaging zones 90 and 92 of IOL optic 82. Transition zone surface 110 is shown as being continuously variably curved, which reduces both indirect and direct glare in the eye of an individual in which IOL 80 is implanted, as more particularly described below.

As shown in FIG. 8, transition zone 94 has a total width, w, which is equal to combined widths, l, and, l' (described below), and a height (depth), h. Width, l, is preferably between about 1.5 times and about 2.0 times a radius, r, of a cutting tool 120 (shown in broken lines). A typical tool radius, r, may be about 0.125 mm, which is sufficiently large to achieve good optical quality of respective first and second imaging zones 90 and 92, while still being sufficiently small to produce a narrow transition zone 94. Accordingly, width, l, is preferably between about 0.14 mm and about 0.27 mm. Assuming, as described below, that width, l', is equal to about 0.1 times width, l, total transition zone width, w, (in the x direction) is preferably between about 0.15 mm and about 0.30 mm. Height, h, (in the z direction) of transition zone 94 is preferably between about 0.10 mm and about 0.40 mm.

As depicted in FIG. 8, transition zone curved surface 110 starts at point 1 at first imaging zone 90 and ends at point 4 at second imaging zone 92, with intermediate surface points 2 and 3.

Radius, $r_1$, of first imaging zone 90 (referring to FIG. 6) prior to point 1 is defined by the following mathematical expression:

$$z = \frac{U_1 X^2}{1 + \sqrt{1 - U_1^2 X^2}}, \tag{1}$$

and its derivative:

$$\frac{dz}{dX} = \frac{U_1 X}{\sqrt{1 - U_1^2 X^2}}, \tag{2}$$

where $$U_1 = \frac{1}{r_1}$$

is the surface curvature, and where z and x are the coordinates from origin, O (as indicated in FIGS. 6 and 8).

Point 2 at transition surface 110 is defined by width, l (from point 1 to the center of tool 120); transition zone height, h; tool radius, r; and tool angle, β, wherein angle, β, is preferably between about 15 degrees and about 20 degrees.

A transition zone surface region 122 between points 1 to 2 connects transition zone 94 with first imaging zone 90, and can be described by the polynomial form of third order as shown below:

$$z = A_1(X-x_1)^3 + B_1(X-x_1)^2 + C_1(X-x_1) + D_1, \tag{3}$$

and its derivative $$\frac{dz}{dX} = 3A_1(X - x_1)^2 + 2B_1(X - x_1) + C_1, \tag{4}$$

where $x_1$ equals the X coordinate at the edge of first imaging zone 90 (that is, half of first imaging zone diameter, $D_2$, shown in FIG. 6).

Point 3 at transition surface 110 is also defined by width, l; transition zone height, h; tool radius, r; and tool angle, β, which is preferably between about 15 degrees and about 20 degrees.

A transition zone surface region 124 between points 2 and 3 is defined by tool radius, r, according to the mathematical expression:

$$z = \frac{U(X - x_1 - l)^2}{1 + \sqrt{1 - U^2(X - x_1 - l)^2}} + C_2, \tag{5}$$

and its derivative:

$$\frac{dz}{dX} = \frac{U(X - x_1 - l)}{1 + \sqrt{1 - U^2(X - x_1 - l)^2}}, \tag{6}$$

where $$U = \frac{1}{r}$$

is the surface curvature

The Z coordinate at transition zone surface point 4 is preferably selected to have the same z value as at surface point 3. Width, l', of a surface region 126 between points 3 and 4 is preferably equal to about 0.10 times width, l, and provides a smooth continuity of transition zone 94 to second imaging zone 92.

Mathematical format of surface region 126 is the same as that of surface region 122 between surface points 1 and 2 and is given by the following expression:

$$z = A_3(X-x_1-l)^3 + B_3(X-x_1-l)^2 + C_3(X-x_1-l) + D_3, \tag{7}$$

and its derivative:

$$\frac{dz}{dX} = 3A_3(X - x_1 - l)^2 + 2B_3(X - x_1 - l) + C_3 \quad (8)$$

Second transition zone 92 of radius, $r_2$, beyond transition surface point 4 is defined by the following mathematical expression:

$$z = \frac{U_2 X^2}{1 + \sqrt{1 - U_2^2 X^2}} + C_4, \quad (9)$$

and its derivative:

$$\frac{dz}{dX} = \frac{U_2 X}{\sqrt{1 - U_2^2 X^2}}, \quad (10)$$

where $$U_2 = \frac{1}{r_2}$$

is surface curvature

All coefficients $A_1$, $B_1$, $C_1$, $D_1$, $C_2$, $A_3$, $B_3$, $C_3$, $D_3$ and $C_4$ defining transition zone equations are calculated by a standard algebraic procedure for continuous border conditions between first imaging zone 90, each transition zone surface region and second imaging zone 92, that is, equal values for z and dz/dX at each border between adjacent surface regions, and also using surface parameters l, l', h, r, $r_1$, and $r_2$.

FIG. 9, which is similar to FIG. 1, depicts a bundle of parallel light rays 112 impinging on anterior surface 114 of optic 82 at angle, α. Light rays 112 are refracted, in accordance with Snell's Law, as they enter, pass through and exit optic 82. However, because of the continuously variable curvature of transition zone surface 110 (FIG. 8), the light exits optic 82 as diverging rays 112a, rather than parallel ays as shown for rays 20a of the prior art Fresnel lens optic 24 depicted in FIG. 1. (Viewed image light rays are not shown to avoid confusion.)

As depicted in FIG. 10, which corresponds to FIG. 2, diverging light rays 112a refracted from transition zone surface 110 of optic 82 impinge on a region 115 of retina 48 (shown in broken lines) of representative eye 30 to cause only a very diffused glare pattern 116 (indicated by dots). The result is that indirect glare in an individual's eye is greatly reduced by the non-abrupt, continuously variable curvature of transition zone surface 110, as compared to the indirect glare in an eye caused by flat surface 38 of abrupt Fresnel zone steps 40 of the same height.

FIG. 11 (which corresponds generally to FIGS. 8 and 9), depicts light rays 112a impinging perpendicularly onto optic anterior surface 114. Due to the particular shape of continuously variably curved transition zone surface 110, as described relative to FIG. 8, light rays 112a' are redirected at surface 110 out of the image by internal reflection.

Although a ray 112a" is depicted in FIG. 11 as refracted from surface 110 in a diverging manner that could cause some image glare, the glare is nevertheless substantially less than the direct glare caused by sharp corners 52 and 54 of Fresnel zone step 38 (FIG. 3) and other Fresnel zone steps of the same height.

The result of transition zone 94 having the continuously variable curved surface 110 described above, is that optic 82 of IOL 80 provided substantially less glare than sharp, flat Fresnel zone step(s) 38.

It is, of course, to be understood that the continuously variable curvature applied to surface 110 of transistion zone 94 of optic 82 can also be applied to surface 110a of transition zone 94a of optic 82a (FIG. 7) with like glare reduction properties.

FIGS. 12 and 13 depict, in extremely enlarged representations, variation transition zone surface curvatures that although providing somewhat less glare reduction than the continually variable curvature described above for surface 110 of transition zone 94 of optic 82 nevertheless are within the scope of the present invention.

There is thus depicted in FIG. 12 a transition zone 94b between respective first and second imaging zones 90b and 92b of an optic 82b. As shown, imaging zones 90b and 92b may be identical to imaging zones 90 and 92 described above. Surface 110b of transition zone 94b is variably curved, but is not continuously variably curved as described above for transition zone surface 110, having, as an example, a discontinuity at a point 130. The variably curved region of transition zone surface 110b may be developed in a manner analogous to the above-described manner of developing transition zone surface 110 (FIG. 8)

A principal effect of variably curved transition zone surface 110b is that some direct glare may be caused by light diffraction at discontinuity point 130 in the manner depicted in FIGS. 3 and 4 for known Fresnel zone step 40.

There is depicted in FIG. 1 a transition zone 94c between respective first and second imaging zones 90c and 92c of an optic 82c. As shown, imaging zones 90c and 92c may be identical to imaging zones 90 and 92 described above. Surface 110c of transition zone 94c is shown continuously curved, but not continuously variably curved as described above for transition zone surface 110, having, as an example, a central region 132 of non-variable curvature a discontinuity at a point 130. The variably curved regions of transition zone surface 110c may be developed in a manner analogous to the above-described manner of developing transition zone surface 110 (FIG. 8)

A principal effect of continuously curved transition zone surface 110c is that some indirect glare may be caused by light refraction from region 132 of surface 110c in the manner depicted in FIGS. 1 and 2 for known Fresnel zone step 40.

Thus it can be seen from the foregoing that a narrow profile intraocular lens with glare reducing characteristics is provided.

Although there has been described above a narrow profile, monofocal intraocular lens with glare reduction and variations thereof for implant in a narrow space, particularly in the anterior chamber, of a patient's eye, in accordance with the present in mention for purposes of illustrating the manner in which the present invention may be used to advantage, it is to be understood that the invention is not limited thereto. Consequently, any and all variations and equivalent arrangements that may occur to those skilled in the applicable art are to be considered to be within the scope and spirit of the invention as set forth in the claims, which are appended hereto as part of this application.

What is claimed is:

1. A narrow profile, glare reducing, phakic anterior chamber intraocular lens comprising:
   a. an optic having an anterior surface and a posterior surface and an optical axis, only said posterior surface being formed having adjacent first and second periaxial imaging zones, said posterior surface being monofocal and refractive;

b. a transition zone between paid first and second peri-axial imaging zones, said transition zone having a height of at least about 0.10 mm and having a surface of continuous curvature without any abrupt change in said surface curvature shaped to minimize direct glare in an individual's eye in which said intraocular lens is implanted by causing internal reflection of light coming from a centrally located source of light within a substantial width of said transition zone; and c. a positioning means joined to said optic for positioning said optic in the anterior chamber of said eye with said optical axis of the optic generally aligned with the optical axis of the eye.

2. The narrow profile, glare reducing, phakic anterior chamber intraocular lens as claimed in claim 1, wherein said transition zone surface has a continuously variable curvature shaped to reduce both indirect and direct glare.

3. The narrow profile, glare reducing, phakic anterior chamber intraocular lens as claimed in claim 1, wherein said first peri-axial imaging zone is centered at the optical axis of the optic.

4. The narrow profile, glare reducing, phakic anterior chamber intraocular lens as claimed in claim 1, wherein said first peri-axial imaging zone is circular in shape, having a diameter between about 4.3 mm and about 4.5 mm and wherein said second peri-axial zone is circular in shape, having a diameter between about 5.5 mm and about 7.5 mm.

5. The narrow profile, glare reducing, phakic anterior chamber intraocular lens as claimed in claim 4, wherein said second peri-axial imaging zone is formed in annular shape around said first peri-axial imaging zone.

6. The narrow profile, glare reducing, phakic anterior chamber intraocular lens as claimed in claim 1, wherein said optic has a maximum thickness at any point that is between about 0.30 mm and about 0.40 mm.

7. The narrow profile, glare reducing, phakic anterior chamber intraocular lens as claimed in claim 1, wherein said optical power is outside a diopter range of about −5 to about +5.

8. The narrow profile, glare reducing, phakic anteriop chamber intraocular lens as claimed in claim 1, wherein the height of said transition zone is between about 0.10 mm and about 0.40 mm.

9. The narrow profile, glare reducing, phakic anterior chamber intraocular lens as claimed in claim 1, wherein said transition zone has a width between about 0.15 mm and about 0.30 mm.

10. A narrow profile, glare reducing, phakic anterior chamber intraocular lens comprising:

a. an optic having an anterior surface and a posterior surface and an optical axis, one of said anterior and posterior surfaces being formed having adjacent first and second peri-axial imaging zones, said posterior surface with peri-axial imaging zones being monofocal and refractive;

b. a transition zone between said first and second peri-axial imaging zones, said transition zone having height of at least about 0.10 mm and having a surface of continuously variable curvature shaped to minimize indirect glare, created by a peripherally located source of light within a substantial width of said transition zone, in an individual's eye in which the intraocular lens is implanted; and c. a positioning means joined to said optic for positioning said optic lens in the anterior chamber of said eye with said optical axis of the optic generally aligned with the optical axis of the eye.

11. The narrow profile, glare reducing, phakic anterior chamber intraocular lens as claimed in claim 10, wherein said first peri-axial imaging zone is centered on the optical axis of the optic and has a diameter between about 4.3 mm and about 4.5 mm and wherein said second peri-axial imaging zone is formed in annular shape around said first peri-axial imaging zone.

12. The narrow profile, glare reducing, phakic anterior chamber intraocular lens as claimed in claim 10, wherein said optic has a maximum thickness at any point no greater than about 0.40 mm.

13. The narrow profile, glare reducing, phakic anterior chamber intraocular lens as claimed in claim 10, wherein said first peri-axial imaging zone is recessed in said optic relative to said second peri-axial imaging zone.

14. The narrow profile, glare reducing, phakic anterior chamber intraocular lens as claimed in claim 10, wherein said second peri-axial imaging zone is recessed in said optic relative to said first peri-axial imaging zone.

15. The narrow profile, glare reducing, phakic anterior chamber intraocular lens as claimed in claim 10, wherein said optical power is outside a diopter range of about −5 to about +5.

16. The narrow profile, glare reducing, phakic anterior chamber intraocular lens as claimed in claim 10, wherein the height of said transition zone is between about 0.10 mm and about 0.40 mm and wherein said transition zone has a width of between about 0.15 mm and about 0.03 mm.

* * * * *